United States Patent [19]

Sweet

[11] 4,319,138
[45] Mar. 9, 1982

[54] HOUSING FOR TURBIDIMETER SENSOR

[75] Inventor: Edmund G. F. Sweet, Oakville, Canada

[73] Assignee: Shaban Manufacturing Ltd., Bolton, Canada

[21] Appl. No.: 127,771

[22] Filed: Mar. 6, 1980

[51] Int. Cl.³ .............................................. G01N 15/06
[52] U.S. Cl. ..................................... 250/576; 356/246
[58] Field of Search .............. 250/573, 574, 575, 576; 356/410, 411, 436, 440, 441, 442, 246, 337–343; 350/319

[56] References Cited

U.S. PATENT DOCUMENTS

| | | | |
|---|---|---|---|
| 3,515,491 | 6/1970 | Emary | 356/246 |
| 3,918,817 | 11/1975 | Posgate | 356/442 |
| 4,250,394 | 2/1981 | O'Connor | 250/576 |

Primary Examiner—David C. Nelms
Attorney, Agent, or Firm—Fetherstonhaugh & Co.

[57] ABSTRACT

A sensor for a fluidimeter where the through flow passage for fluid is embedded in a plastics material to support it against fracture due to high pressure in the fluid flow passage.

11 Claims, 3 Drawing Figures

HOUSING FOR TURBIDIMETER SENSOR

This invention generally relates to a sensor for measuring the relative amounts of light passing through a fluid and reflected by particles suspended in the fluid. In use, signals from the sensor are fed into an associated instrument in which they are inter-related and magnified to produce direct and continuous measurement of properties of the fluid such as turbidity. More particularly, the invention is concerned with improvements in the sensor construction and the method of constructing the sensor that make it possible to use the sensor at fluid working pressures in the order of 50 to 150 pounds per square inch as commonly encountered in industrial processes and to achieve accurate results. Sensors of the prior art vary considerably depending upon the specific use for which they are designed. Most of them are not capable of measuring fluids at pressures in the order of 50 to 150 p.s.i.

The commonly used sensor that is capable of measuring fluids at these higher pressures has a metalic body with a through flow passage for fluid to be tested. The optical components are mounted in passages that extend from the through flow passage that conducts the fluid and the lenses or windows are sealed in the passages. The construction is very expensive and also suffers from the disadvantage that the lens must be mounted in spaced relation to the through passage that conducts the fluid. The portion of the lens passage between the through passage and the lens tends to collect sediment from the fluid passing through on a continuous basis. The collection of this sediment causes inaccuracies in the reading. Thus, these instruments are both expensive and less accurate than this invention.

Measurements of fluidity on a continuous basis have also been made by mounting a glass cuvet within an enclosed casing, passing a beam of light through the cuvet and measuring the reflected beam as an indication of turbidity. The fluid to be measured is passed through the cuvet on a continuous basis so that the instrument is, to this extent, capable of making a continuous measurement of turbidity. However, the glass cuvet is located with its walls in spaced relation to the walls of the casing and it is not possible with this device to pass fluid through the cuvet at pressures in the order of 50 to 150 p.s.i. Such pressures would break the glass cuvet. Thus, the use of the unsupported glass cuvet is limited to cases where the pressure is in the order of atmospheric pressure and cannot be used on a continuous basis in industrial processes where the fluid pressure is high.

A further method of taking a continuous measurement of turbidity that has been used is to mount a glass tube within a casing and seal it at its ends and then pass the fluid whose turbidity is to be measured through the glass tube on a continuous basis. An optical system within the casing directs a beam of light through the tube and measurements of the reflected light are taken as an indication of turbidity. In this device the glass tube is unsupported and tends to break at relatively low pressures. The tendency of the glass tubing to break cannot be avoided in practice by increasing the thickness of the wall of the glass tubing because increased thickness of the tubing distorts the optical qualities of the beam of light that is used to measure turbidity.

The present invention provides an inexpensive accurate sensor assembly that can be used at the higher pressures encountered in industrial processes on a continuous basis. A sensor for a fluid meter according to this invention has:

a body having a fluid flow channel therethrough; said fluid flow channel including a translucent tube; said translucent tube being supported externally in a light absorbing plastic casting compound, the said plastic compound adhering to the exterior of the tube whereby to support it as aforesaid; light channels through said casting compound terminating at said translucent tube for passing light to and from the interior of the tube whereby to measure the turbidity of fluid in the tube; said light channels having a cross-sectional area at said tube that is small; the fracture pressure of the tube wall at said light channels being greater than the rated fluid flow pressure through the fluid flow channel. The body of the sensor according to the invention is made by the steps of: forming a casing; supporting casting plugs in the casing to form a fluid flow channel therethrough and light channels that terminate at said fluid flow channels. The invention will be clearly understood after reading the following detailed specification in conjunction with the drawings.

Figure 1:
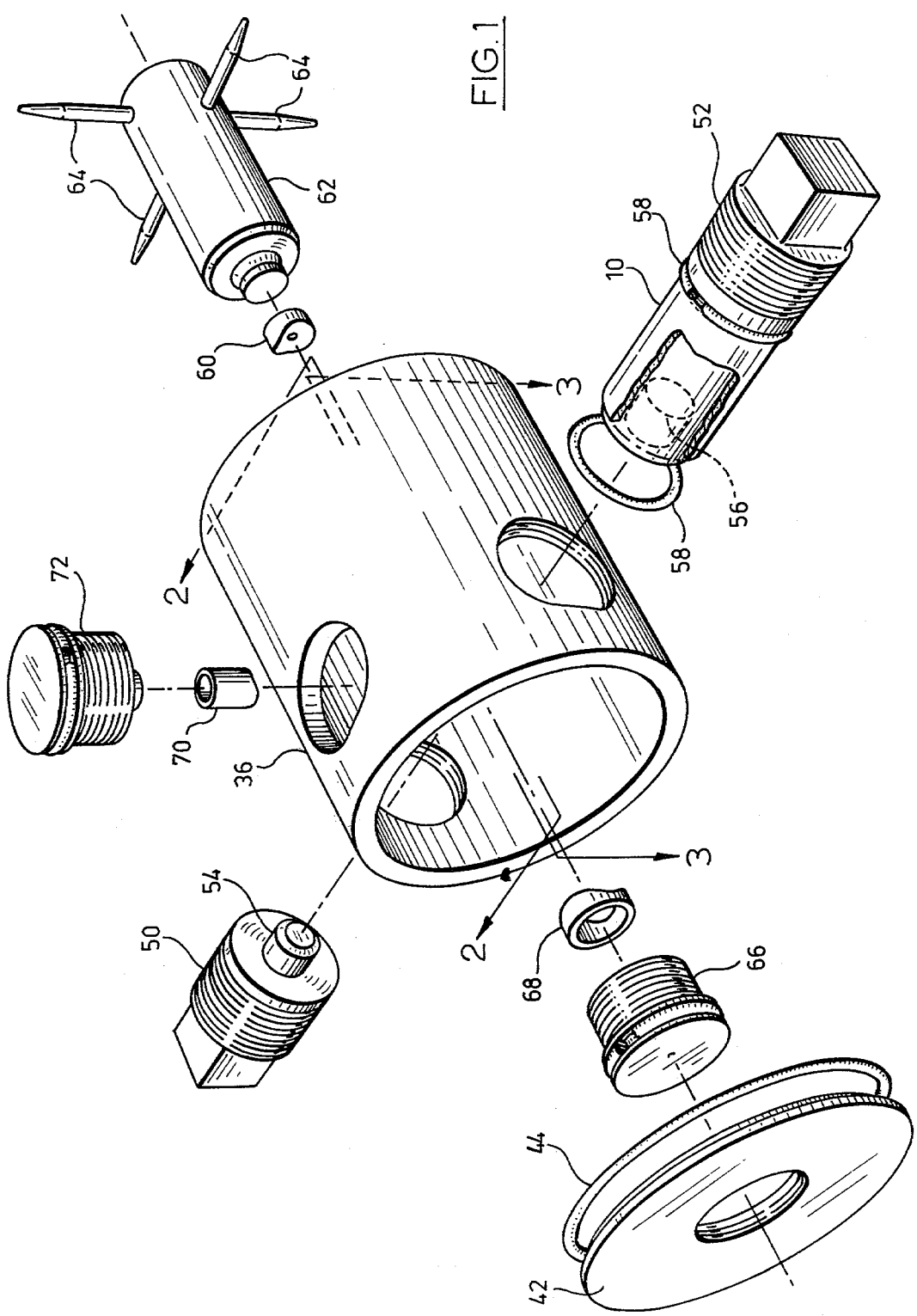
FIG. 1 is an illustration of the outer walls and casting plugs used in the manufacture of a sensor according to this invention.
Figure 2:
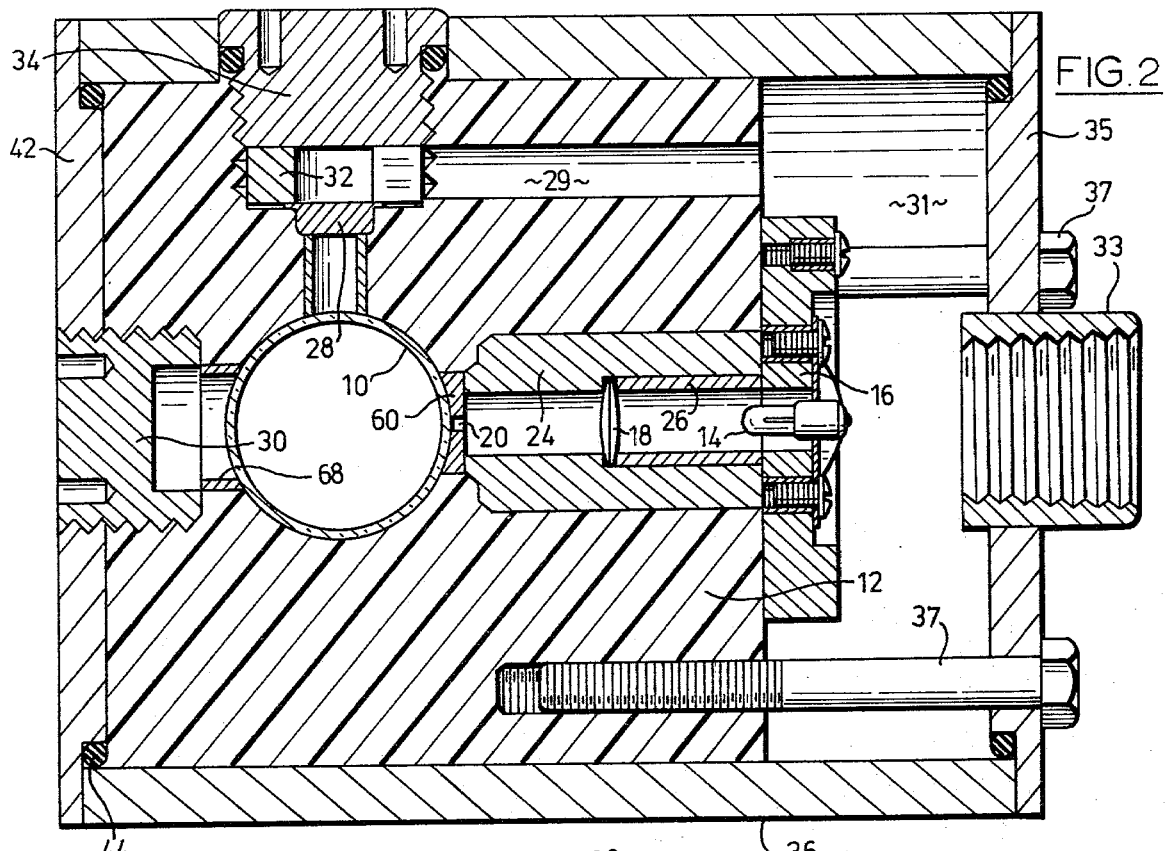
FIG. 2 is a sectional view of a sensor with an electrical and optical system installed, taken along the line 2—2 of the casing of FIG. 1.
Figure 3:
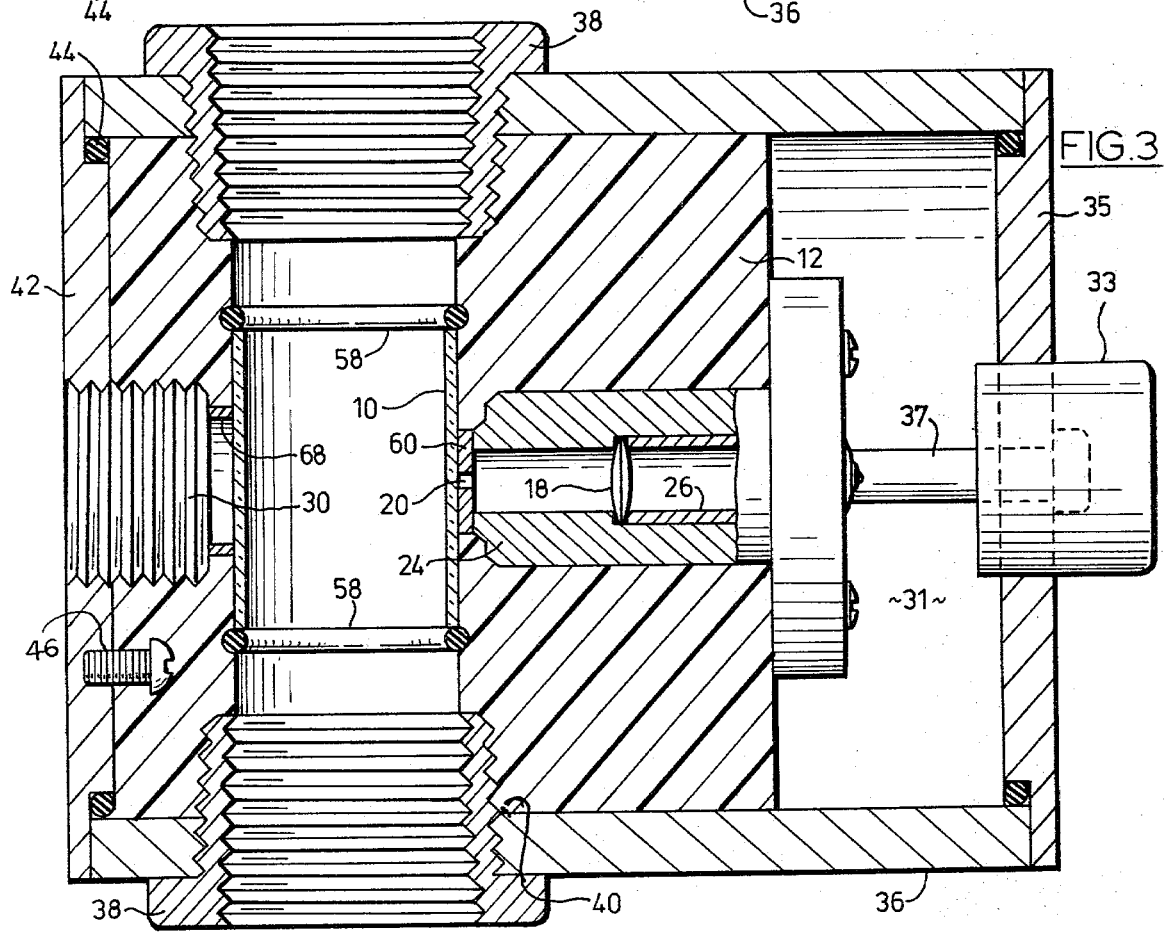
FIG. 3 is a sectional view similar to FIG. 2 but taken along the line 3—3 of FIG. 1.

The embodiment of the invention illustrated is a fluidimeter for measuring the turbidity of fluids on a continuous basis. The optical and electrical arrangement of the parts is illustrated in FIG. 2. The fluid whose turbidity is to be measured on a continuous basis through a glass tube 10 which is embedded in a body of opaque plastics compound 12. A light bulb 14 appropriately supported in a lamp support assembly 16 is rigidly mounted with respect to the body of plastics material 12 so that light eminating from the bulb 14 is focused by means of lens 18 into a narrow beam that passes through slit 20, the wall of translucent tube 10 and a fluid passing through the tube. Lens 18 is retained within the sleeve 24 by means of the lens retaining sleeve 26.

In use, light from the source lamp 14 is concentrated by lens 18 and passes into the tube 10 through the slit 20. The device is designed to give an indication of the turbidity of the fluid passing through the tube 10 and it does this by measuring the amount of light reflected by particles from the beam onto a photodiode 28. Photodiode 28 measures the reflected light through an electronics circuit and gives a quantitative reading of the turbidity of the fluid as it passes the light beam that eminates from the light source 14.

Numeral 30 is a reflected light plug or light trap for the purpose of diminishing the affect of reflective light in the reading.

Diode 28 is maintained in position by means of spacer 32 and retaining nut 34.

The body of plastics material is light absorbing and does not, therefore, reflect appreciable light back into the tube that is likely to cause errors in the reading. The electronics of the unit are not fully illustrated. They include wiring that extends from the photodiode, through channel 29 into housing 31 and out fitting 33 for connection to appropriate metering dials. The cover 35 for the unit 4 is retained in place by bolts 37 that extend into the plastics material 12.

There is nothing novel about the optical and electronics circuits of the meter. The illustration of these components is merely by way of explanation of the embodiment of the invention illustrated. The invention, as indicated in the preamble, is concerned with the sensor for maintaining the optical and electronics parts in operative relation and the method of making it.

The sensor illustrated has a tubular steel sidewall 36 having a diameter of about 4 inches. Fluid input and output bushings 38 are tack welded to the wall of the sensor as at 40 and in use fluid connection is made to these bushings for the purpose of passing fluid through the unit on a continuous basis.

The fluid channel through the body of plastics material 12 includes a length of borosilicate glass tubing 10 having an outside diameter of about 1⅛ inches, a wall thickness of about 1/16 of an inch and a length of about 1½ inches. The qualities of this glass tubing are such that light will pass through it for the purpose of making the necessary measurements without undue distortion. It has a low coefficient of expansion and can withstand wide temperature fluctuation.

End plate 42 is sealed at the inside wall of the tube 36 with an O-ring 44 and retained rigid with respect to the side wall by means of screws 46 which are lockedly embedded in the body of plastic material 12.

The general method of making the sensor body is to support the glass tube 10 and molding plugs to form the necessary openings in the body of plastics material 12 in a hollow shell that is comprised of the tubular side wall 36 and the end wall 42, prepare a liquid plastics filler preparation, pour it into the open end of the shell, let is cure to form the body of plastics material 12, and remove the removable molding plugs from the unit so that the operating parts can be mounted therein.

This general method is carried out by first tack-welding bushings 38 as at 40 into the diametrically opposed openings in the steel side wall 36. The glass tube 10 is slid over the shank of plug 52 with O-rings 58 at each end. Plug 52 and plug 50 are then threaded through the interior threads of the bushings 38 and 40 to cause the pin 54 of plug 50 to enter the cavity 56 of plug 52 and compress the tube 10 between the O-rings 58. Thus, the glass tube 10 is supported within the tubular side wall 36 and the plugs 50 and 52 are located to form the through passage way for fluid after the molding operation is completed.

The opening 20 for the beam of light that passes through the lens 18 of the optical system is through a molding insert 60. This insert is held firmly in place against the side of the tube 10 by means of a molding plug 62 which is in turn held in place within the tubular side wall 36 by means of spacing bars 64. It will be noted that the end of the plug 62 that engages with the glass tube 10 is accurately formed to closely abut the tube and prevent any molding material from entering the space between the tube and the plug.

Bottom plate 42 has an O-ring seal 44 around its edge and is press fitted into one end of the open side wall 36. It has a plug 66 screw threaded through its central opening to force plug 68 against the glass tube 10 to form the entrance to the reflection well 30.

A plug 72 threaded as illustrated is inserted into the top opening in the tubular side wall and has a boss on the free end thereof that presses the plug 70 into contact with the glass tube.

The unit with the plugs arranged as described is then stood on the end wall 42 and a liquid thermosetting plastics material is prepared and poured into the open end of the tubular side wall to a level below the spacing bars 64 of the plug 62. This is the body of plastics material 12.

When the body of plastics material 12 has cured plugs 62, 72, 50, 52 and 66 are removed. These plugs are made from a material such as Teflon that does not adhere to the body of cured molding material 12. The plugs 60, 70 and 68 remain in the unit. These plugs are made from a material such as nylon which does adhere to the body of cured molding material 12. They are permanently located.

Thus, on the completion of the molding operation and removal of the removable plugs the basic sensor body construction is formed. There is a through fluid flow passage between the bushings 38 that includes the glass tube 10. The necessary window openings from the tube are formed. It will be noted that the O-rings 58 which are designed to prevent plastic material from getting on the inside of the tube remain in the body of material.

The light passage 20 is formed within the plug 60 and the sleeve 24 that mounts the lens and the lamp support assembly is mounted within the cavity left by the plug 62. The reflected light plug or light trap 30 is mounted in the body within the cavity left by the plug 66 and the diode 28 spacer 32, and plug 34 are mounted within the cavity left by the space provided by the removal of plug 72. Machining of the body of molded material is carried out to provide for accurate forming of these parts.

A variety of casting resins can be used. The important features of the resin are that it be able to encapsulate the glass tube 42 without noticeable shrinkage as it cools so that on curing it adheres to the exterior of the tube and supports it externally except at the location of the apertures formed by the plugs 60, 68 and 70.

As indicated it is important that the glass tube 10 be supported externally except at the apertures because this external support is necessary to give the glass tube support against high pressure fluids that will flow through it in use. If there is space between the tube and the body of plastics material 12 the tube will tend to fracture at higher operating pressures.

There is no support for the tube at the location of the aperture for the optical system, the light trap and the diode recess, but the areas of these apertures are small to that the fracture pressure of the tube wall at the apertures is greater than the rated fluid flow pressure through the fluid flow channel.

In the embodiment illustrated the largest aperture at tube 68 is round and about ⅝" in diameter. This does not fracture at pressures exceeding 300 p.s.i. fluid pressure. Thus, such an instrument is safely rated at 150 p.s.i. fluid pressure.

It will be apparent that the fracture pressure of the tube wall at the apertures will vary with the thickness of the glass. The thickness of the glass used in the embodiment illustrated is 1/6". A thicker glass would withstand more pressure for a given aperture size. However, there is a limit to the thickness of the glass for optical reasons.

It has been found that casting to support the outer wall of the tube is the only practical way to support the tube against breakage for high flow pressures. If, for example, one were to bore a body of plastic and insert the tube in the bore the necessary clearance for the purpose of inserting the glass tube would involve a spacing between the glass and the plastics material that would result in breakage of the tube. With the present invention the plastics compound adheres to the tube and supports it fully against breakage at high operating pressures.

The casting material 12 can conveniently be a two component, semi-rigid, filled epoxy potting and casting compound with low water absorption, able to stand temperatures of between 32° and 100° F., have low shrinkage on curing, have good adhesion characteristics to metal and glass surfaces to provide support and a permanent liquid proof seal, have a low exothermic and relatively long cure time with a view to achieving minimum shrinkage and permanent adhesion, be able to accept black colouring to eliminate light reflection, be machinable after curing, and be free of porosity to insure water tight service.

Suitable for the purpose has been found the two component semi-rigid filled apoxy potting and casting compound the base being Conapoxy FR-1210 and the hardener being Conacure EA-87. Conapoxy and Conacure are trade marks of Conap Inc. of Olean, N.Y., U.S.A. Such a resin when mixed 100 parts FR-1210 by weight to 18.5 parts EA-87 gives a product with an initial mixed viscosity of about 4100 cps at 25° C. The mixture cures in between 24 and 48 hours at 25° C. and in about 2 hrs. at 60° C. It has a shore hardness of 90±5 and a linear shrinkage of 0.41%.

Embodiments of the invention other than the one illustrated will be apparent to those skilled in the art. More complex electronics and optical arrangements are possible some of which will involve different detectors and some of which will involve more passages through the body of material 12 to the tube 10. The shape of the tube 10 can vary and in particular it is contemplated that the tube 10 can be flattened to have a very short cross-dimension at the aperture 20 that could be useful in measuring fluids of high turbidity. It is contemplated that the dimension across the tube at the window 20 might be in the order of 10 millimeters for measuring a dense fluid. A cross section of the tube in the nature of a rectangle would be very weak unless supported by the body of plastics material 12.

The shell arrangment within which the plastics body 12 is contained is capable of great variation and not restricted to the construction illustrated. An important feature of the invention is the supporting of the crystaline glass tube through which the fluid whose turbidity is to be measured be supported in a body of plastics material 12 to insure against fracture at higher operating pressures.

The tube 10 is crystaline and subject to fracture. While glass is the obvious and only practical crystaline substance known to the inventor, it is contemplated that other fractionable crystaline substances may be used. The invention is concerned with the support of a translucent crystaline substance against fracture where the substance will fracture at less than the pressure of the fluid passing through the meter.

The embodiments of the invention in which an exclusive property or privilege is claimed are defined as follows:

1. A sensor for a fluidimeter comprising:
   a body having a fluid flow channel therethrough;
   said fluid flow channel including a translucent tube of crystaline material;
   said translucent tube of crystaline substance being supported externally in a light absorbing plastics casting compound, the said plastics compound adhering to the exterior of the tube;
   light channels through said casting compound terminating at said translucent tube for passing light to and from the interior of the tube wherein to measure the turbidity of the fluid in the tube;
   said light channels having a cross sectional area at said tube that is small, the fracture pressure of the tube wall at the light channels being greater than the rated fluid flow pressure through the fluid flow channel.

2. A sensor for a fluidimeter as claimed in claim 1 wherein said light channels adjacent said translucent tube are formed from a plastics material that is cast into said plastics casting compound.

3. A sensor for a fluidimeter as claimed in claim 1 wherein said body has a preformed side wall and a preformed end wall that contain said opaque plastics casting compound.

4. A sensor for a fluidimeter as claimed in claim 1 wherein said light channels comprise a channel adapted to contain a light source, a channel to conduct reflected light to a light sensing system and a channel aligned with the channel of said light source to absorb reflective light.

5. A sensor as claimed in claim 1 in which the fracture pressure of the tube wall at the light channels is above 50 p.s.i.

6. A sensor as claimed in claim 1 in which the fracture pressure of the tube wall at the light channels is above 150 p.s.i.

7. A sensor as claimed in claim 1 in which said tube is glass.

8. A sensor as claimed in claim 2 in which said tube is glass.

9. A sensor as claimed in claim 3 in which said tube is glass.

10. A method of making a fluidimeter body comprising
    forming a casing;
    supporting casting plugs in said casing to form a fluid flow channel therethrough and light channels that terminate at said fluid flow channel;
    said plug for said flow channel including a transparent tube of a crystaline substance the interior wall of which will define at least a proportion of said fluid flow channel;
    said light channels terminating as aforesaid at the interior wall of said tube;
    and pouring a liquid plastics material into said casing to cover said casing plugs;
    permitting said plastics material to cure and removing said casting plugs to form a fluid flow channel wherein said outer surface of said transparent tube is fully supported by said body of plastics material and wherein said light channels terminate at said fluid flow channel.

11. A method of making a fluidimeter body as claimed in claim 10 wherein said transparent tube is glass having low expansion characteristics.

* * * * *